US009976961B2

(12) United States Patent
Maruyama et al.

(10) Patent No.: US 9,976,961 B2
(45) Date of Patent: *May 22, 2018

(54) SURFACE-ENHANCED RAMAN SCATTERING ELEMENT INCLUDING A CONDUCTOR LAYER HAVING A BASE PART AND A PLURALITY OF PROTUSIONS

(71) Applicant: HAMAMATSU PHOTONICS K.K., Hamamatsu-shi, Shizuoka (JP)

(72) Inventors: Yoshihiro Maruyama, Hamamatsu (JP); Katsumi Shibayama, Hamamatsu (JP); Masashi Ito, Hamamatsu (JP); Toru Hirohata, Hamamatsu (JP); Hiroki Kamei, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/420,404

(22) PCT Filed: Aug. 9, 2013

(86) PCT No.: PCT/JP2013/071699
§ 371 (c)(1),
(2) Date: Feb. 9, 2015

(87) PCT Pub. No.: WO2014/025030
PCT Pub. Date: Feb. 13, 2014

(65) Prior Publication Data
US 2015/0211999 A1 Jul. 30, 2015

(30) Foreign Application Priority Data

Aug. 10, 2012 (JP) ................................ 2012-178767

(51) Int. Cl.
*G01N 21/65* (2006.01)
*B82Y 40/00* (2011.01)

(52) U.S. Cl.
CPC ............ *G01N 21/658* (2013.01); *B82Y 40/00* (2013.01); *G01N 2201/068* (2013.01)

(58) Field of Classification Search
CPC ...... G01N 21/65; G01N 21/658; B82Y 15/00; B82Y 40/00
See application file for complete search history.

(56) References Cited

U.S. PATENT DOCUMENTS

2004/0023046 A1 2/2004 Schlottig et al.
2006/0061762 A1* 3/2006 Dwight .................. B82Y 30/00
356/301

(Continued)

FOREIGN PATENT DOCUMENTS

CN 101057132 10/2007
CN 101281133 10/2008

(Continued)

OTHER PUBLICATIONS

"Q-SERS™ G1 Substrate," Opto Science, Inc. (retrieved on-line on Jul. 5, 2013).

(Continued)

*Primary Examiner* — Kara E Geisel
*Assistant Examiner* — Violeta A Prieto
(74) *Attorney, Agent, or Firm* — Drinker Biddle & Reath LLP

(57) ABSTRACT

A SERS element comprises a substrate; a fine structure part formed on a front face of the substrate and having a plurality of pillars; and a conductor layer formed on the fine structure part and constituting an optical function part for generating surface-enhanced Raman scattering. The conductor layer has a base part formed along the front face of the substrate and a plurality of protrusions protruding from the base part at respective positions corresponding to the pillars. The base part and the protrusions form a plurality of gaps in the (Continued)

conductor layer, each of the gaps having an interstice gradually decreasing in the projecting direction of the pillar.

8 Claims, 13 Drawing Sheets

(56) References Cited

U.S. PATENT DOCUMENTS

| | | | |
|---|---|---|---|
| 2006/0146323 | A1 | 7/2006 | Bratkovski et al. |
| 2008/0094621 | A1 | 4/2008 | Li et al. |
| 2008/0218761 | A1 | 9/2008 | Nishikawa et al. |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2014/0043605 | A1 | 2/2014 | Tseng et al. |
| 2014/0045209 | A1* | 2/2014 | Chou ............ G01N 21/6452 435/34 |
| 2015/0212000 | A1* | 7/2015 | Maruyama ........ G01N 21/658 356/244 |
| 2015/0212002 | A1* | 7/2015 | Ito .................. G01N 21/658 359/241 |
| 2015/0212003 | A1* | 7/2015 | Shibayama ....... G01N 21/658 356/244 |
| 2015/0219562 | A1* | 8/2015 | Shibayama ....... G01N 21/658 356/244 |
| 2015/0233832 | A1* | 8/2015 | Maruyama ........ G01N 21/658 356/244 |
| 2015/0233833 | A1* | 8/2015 | Shibayama ....... G01N 21/658 356/244 |

FOREIGN PATENT DOCUMENTS

| | | |
|---|---|---|
| CN | 101319994 | 12/2008 |
| CN | 102282094 | 12/2011 |
| CN | 102483354 | 5/2012 |
| EP | 2278301 | 1/2011 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012-233707 A | 11/2012 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

International Search Report dated Nov. 12, 2013, issued in International Application No. PCT/JP2013/071695.

International Search Report dated Nov. 5, 2013, issued in International Application No. PCT/J P2013/071696.

International Search Report dated Nov. 5, 2013, issued in International Application No. PCT/JP2013/071699.

International Search Report dated Nov. 5, 2013, issued in International Application No. PCT/J P2013/071700.

International Search Report dated Nov. 19, 2013, issued in International Application No. PCT/JP2013/071702.

International Search Report dated Nov. 12, 2013, issued in International Application No. PCT/J P2013/071703.

International Search Report dated Nov. 5, 2013, issued in International Application No. PCT/JP2013/071709.

International Search Report dated Nov. 5, 2013, issued in International Application No. PCT/JP2013/071710.

International Search Report dated Apr. 28, 2014, issued in International Application No. PCT/JP2014/052926.

International Search Report dated May 13, 2014, issued in International Application No. PCT/JP2014/052928.

English Machine Translation of JP 2011-107032, Nishikawa et al., Jun. 2, 2011 as attached to U.S. Office Action dated Oct. 14, 2016 in U.S. Appl. No. 14/420,510.

U.S. Office Action dated Dec. 14, 2015 that issued in U.S. Appl. No. 14/420,422 including Double Patenting Rejections on pp. 8-11.

U.S. Office Action dated Oct. 14, 2016 that issued in U.S. Appl. No. 14/420,510 including Double Patenting Rejections on pp. 2-14.

W. Zhang et al., "Giant and uniform fluorescence enhancement over large areas using plamonic nanodots in 3D resonant cavity nanoantenna by nanoimprinting", Nanotechnoigy. vol. 23, No. 22, May 10, 2012, p. 225301, XP020224099.

S. M. Wells et al., "Efficient disc on pillar substrates for surface enhanced Raman spectroscomyr", Chemical Communications—Chemcom, vol. 47, No. 13, Jan. 1, 2011, p. 3814-p. 3816, XP055289549.

K. Nakamoto et al., "Arrays of Metallic Nanopillars in Holes for Plasmonic Devices", Retrieved from the Internet: URL: http://www.rsc.org/images/LOC/2011.PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show—NSTI Nanotech, vol. 1. May 11, 2006, p. 58-p. 61, XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

\* cited by examiner

Fig.6
(a)
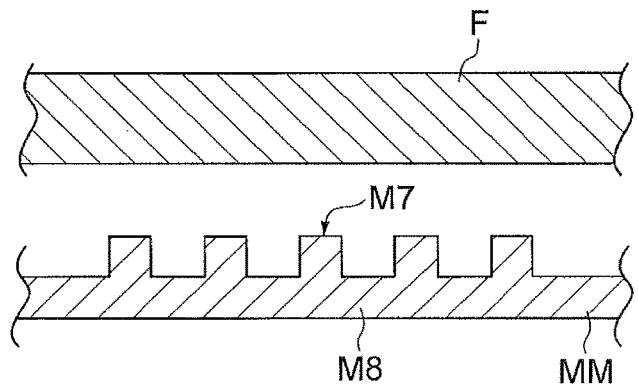
(b)
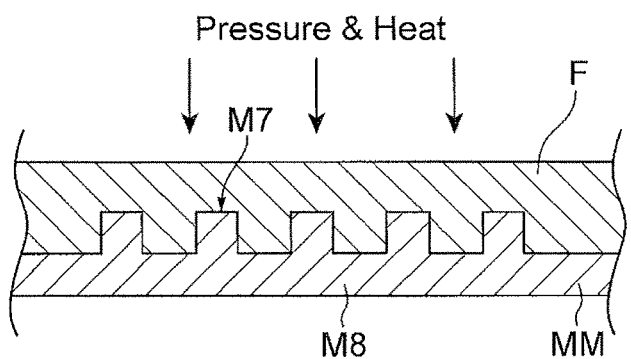
(c)
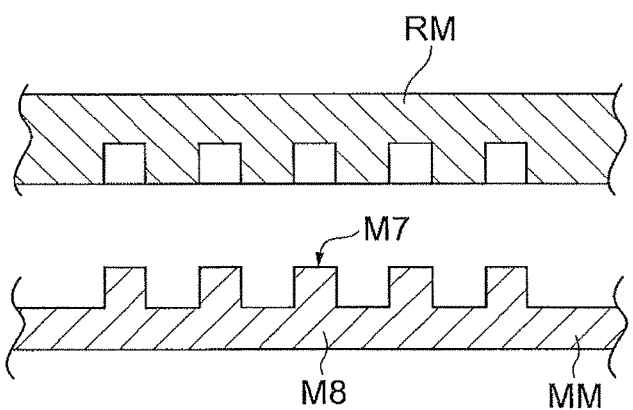

*Fig.7*
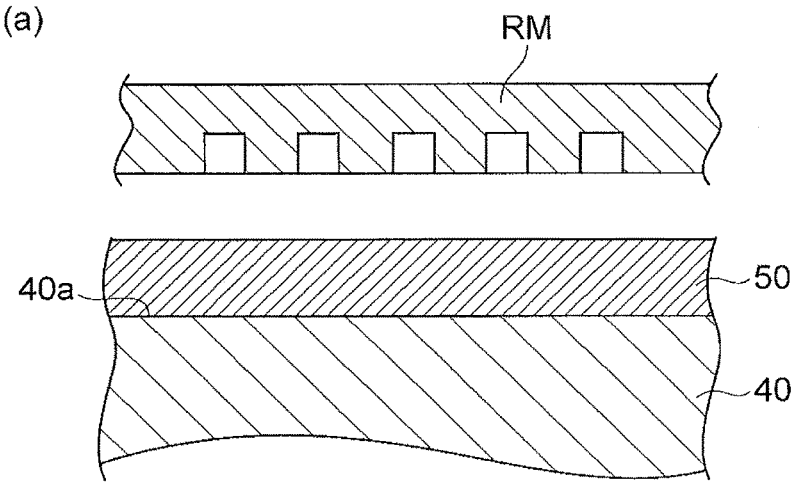
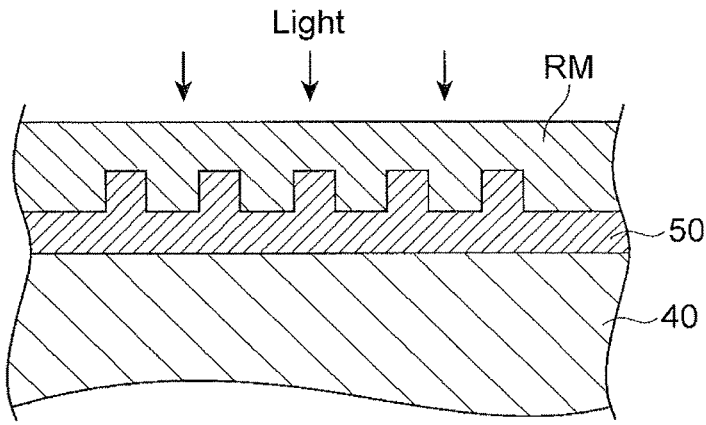
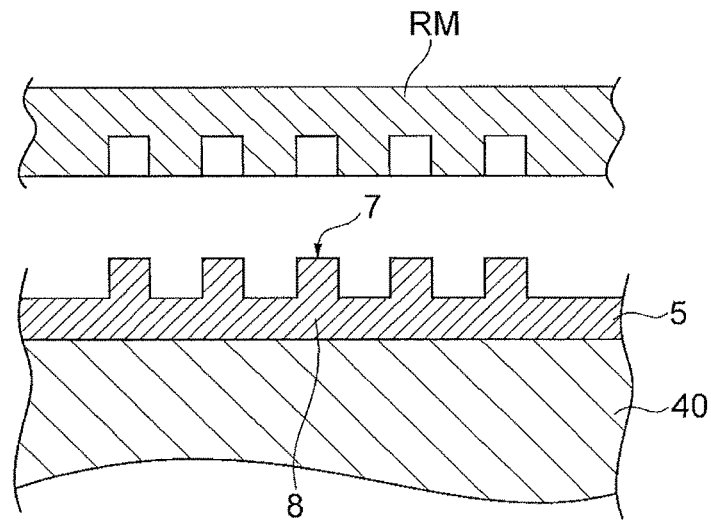

50nm

Fig.9
(a)
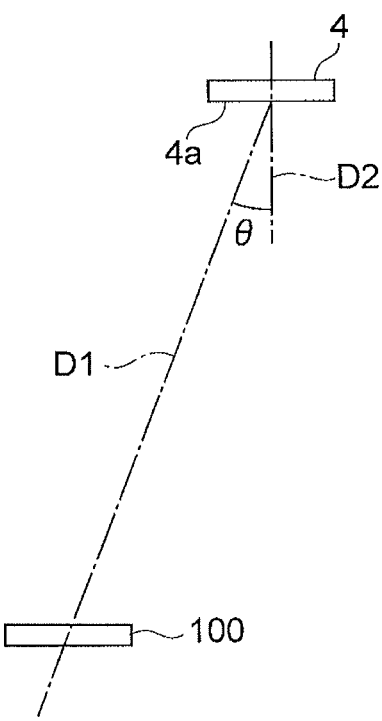
(b)
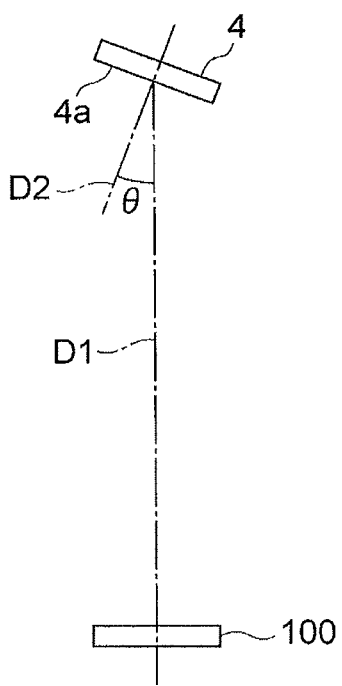

SURFACE-ENHANCED RAMAN SCATTERING ELEMENT INCLUDING A CONDUCTOR LAYER HAVING A BASE PART AND A PLURALITY OF PROTUSIONS

TECHNICAL FIELD

The present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1). In such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a minute metal structure in which metal layers are formed on one surface of a substrate and upper faces of a plurality of minute projections formed on the one surface of the substrate (or bottom faces of a plurality of fine holes formed on the one surface of the substrate) so as to be out of contact with each other (such that the shortest distance therebetween is on the order of 5 nm to 10 μm).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved on 2012 Jul. 19]. Retrieved from the Internet: <URL: http://www.optoscience.com/maker/nanova/pdf/Q-SERS_G1.pdf>.

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases.

It is therefore an object of the present invention to provide a surface-enhanced Raman scattering element which can increase the intensity of surface-enhanced Raman scattering by a favorable nanogap.

Solution to Problem

The surface-enhanced Raman scattering element in accordance with one aspect of the present invention comprises a substrate having a principal surface; a fine structure part formed on the principal surface and having a plurality of projections; and a conductor layer formed on the fine structure part and constituting an optical function part for generating surface-enhanced Raman scattering; the conductor layer having a base part formed along the principal surface and a plurality of protrusions protruding from the base part at respective positions corresponding to the projections; the base part and protrusions forming a plurality of gaps in the conductor layer, each of the gaps having an interstice gradually decreasing in the projecting direction of the projections.

In this surface-enhanced Raman scattering element, the base part and protruding parts form a plurality of gaps, each of the gaps having an interstice gradually decreasing in the projecting direction of the projections, in the conductor layer constituting the optical function part. The gaps formed in this conductor layer favorably function as nanogaps where electric fields are enhanced. Therefore, this surface-enhanced Raman scattering element can increase the intensity of surface-enhanced Raman scattering by favorable nanogaps.

In the surface-enhanced Raman scattering element in accordance with one aspect of the present invention, the projections may be arranged periodically along the principal surface. This configuration can increase the intensity of surface-enhanced Raman scattering.

In the surface-enhanced Raman scattering element in accordance with one aspect of the present invention, the gaps may be formed along a part of the respective projections and each of the gaps may have the interstice gradually decreasing at both end parts when seen in the projecting direction of the projections. This configuration can increase the gaps favorably functioning as nanogaps.

In the surface-enhanced Raman scattering element in accordance with one aspect of the present invention, the gaps may be arranged on the same side of the projections corresponding thereto. This configuration can selectively increase the intensity of light having a predetermined polarization direction.

In the surface-enhanced Raman scattering element in accordance with one aspect of the present invention, the interstice of the gap may gradually decrease continuously. This configuration enables the gaps formed by the base part and protrusions to function securely as nanogaps.

In the surface-enhanced Raman scattering element in accordance with one aspect of the present invention, the protrusion may have a form constricted at an end part on the substrate side. This configuration can easily and securely yield the gap gradually decreasing the interstice in the projecting direction of the projections.

In the surface-enhanced Raman scattering element in accordance with one aspect of the present invention, the base part may have a thickness either smaller or greater than a height of the projections. Either configuration can increase the intensity of surface-enhanced Raman scattering by favorable nanogaps.

Advantageous Effects of Invention

The present invention can provide a surface-enhanced Raman scattering element which can increase the intensity of surface-enhanced Raman scattering by a favorable nanogap.

BRIEF DESCRIPTION OF DRAWINGS

FIG. 6 is a sectional view illustrating steps of manufacturing the surface-enhanced Raman scattering element of FIG. 1;

FIG. 7 is a sectional view illustrating steps of manufacturing the surface-enhanced Raman scattering element of FIG. 1;

FIG. 9 is a structural diagram illustrating a vapor deposition step of the surface-enhanced Raman scattering element of Example 1;

DESCRIPTION OF EMBODIMENTS

Figure 1:
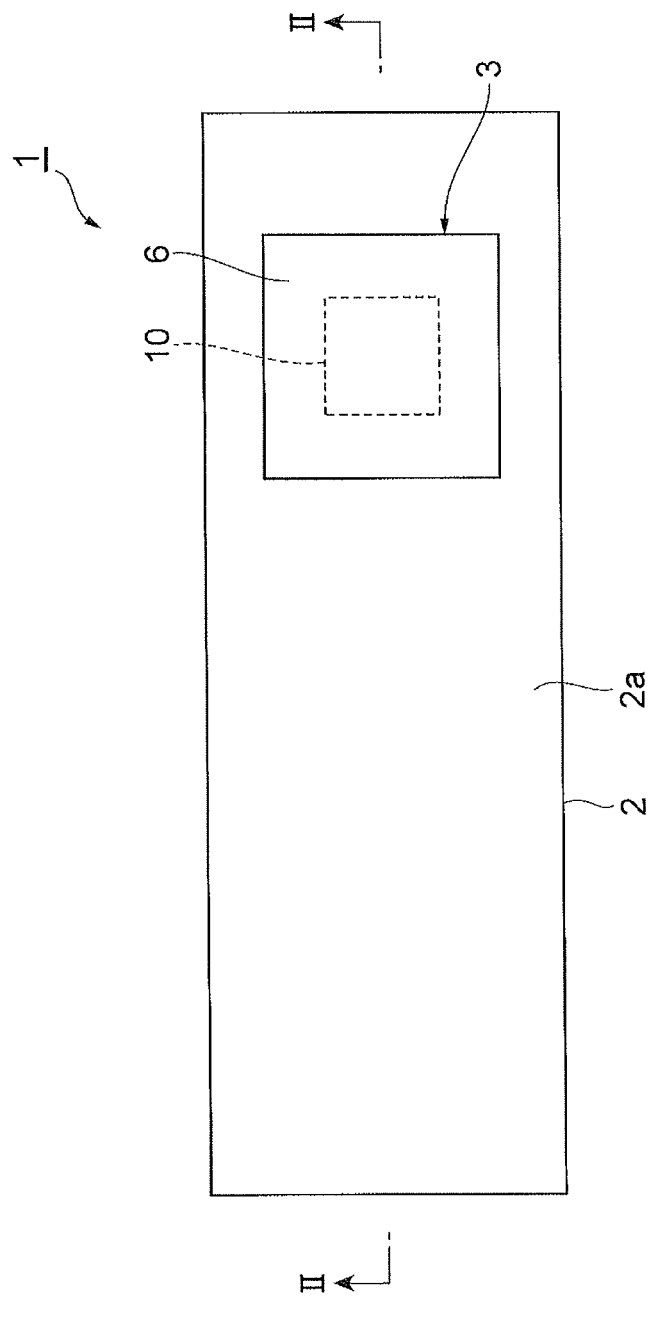
FIG. 1 is a plan view of a surface-enhanced Raman scattering unit equipped with a surface-enhanced Raman scattering element in accordance with an embodiment of the present invention.

In the following, preferred embodiments of the present invention will be explained in detail with reference to the drawings. In the drawings, the same or equivalent parts will be referred to with the same signs while omitting their overlapping descriptions.

Figure 2:
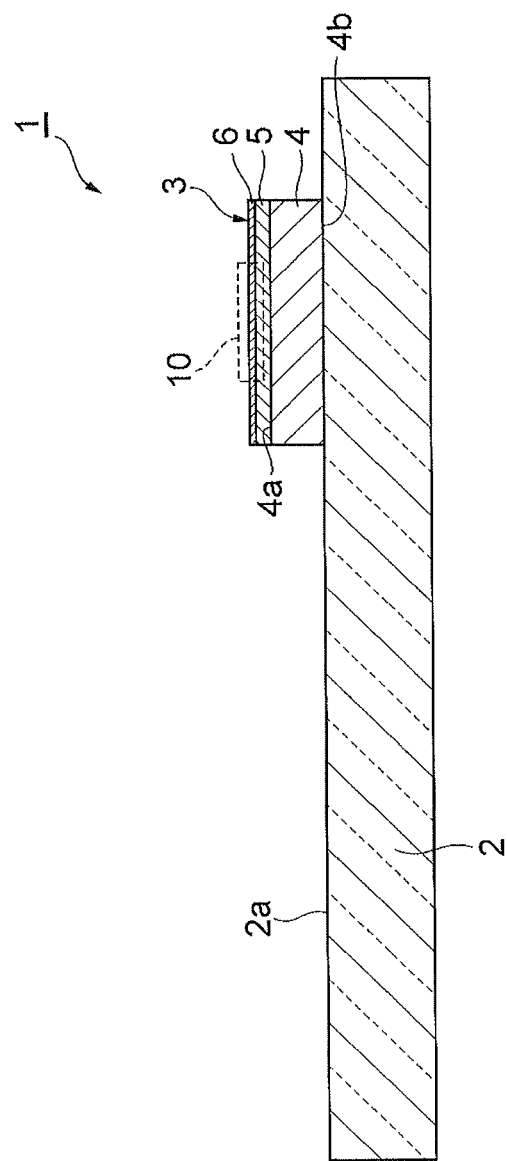
FIG. 2 is a sectional view taken along the line of FIG. 1.

As illustrated in FIGS. 1 and 2, a SERS unit (surface-enhanced Raman scattering unit) 1 comprises a handling board 2 and a SERS element (surface-enhanced Raman scattering element) 3 attached onto the handling board 2. The handling board 2 is a rectangular plate-shaped glass slide, resin board, ceramic board, or the like. The SERS element 3 is arranged on a front face 2a of the handling board 2 while being biased to one end part in the longitudinal direction of the handling board 2.

The SERS element 3 comprises a substrate 4 attached onto the handling board 2, a molded layer 5 formed on the substrate 4, and a conductor layer 6 formed on the molded layer 5. The substrate 4 is formed into a rectangular plate by silicon, glass, or the like and has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
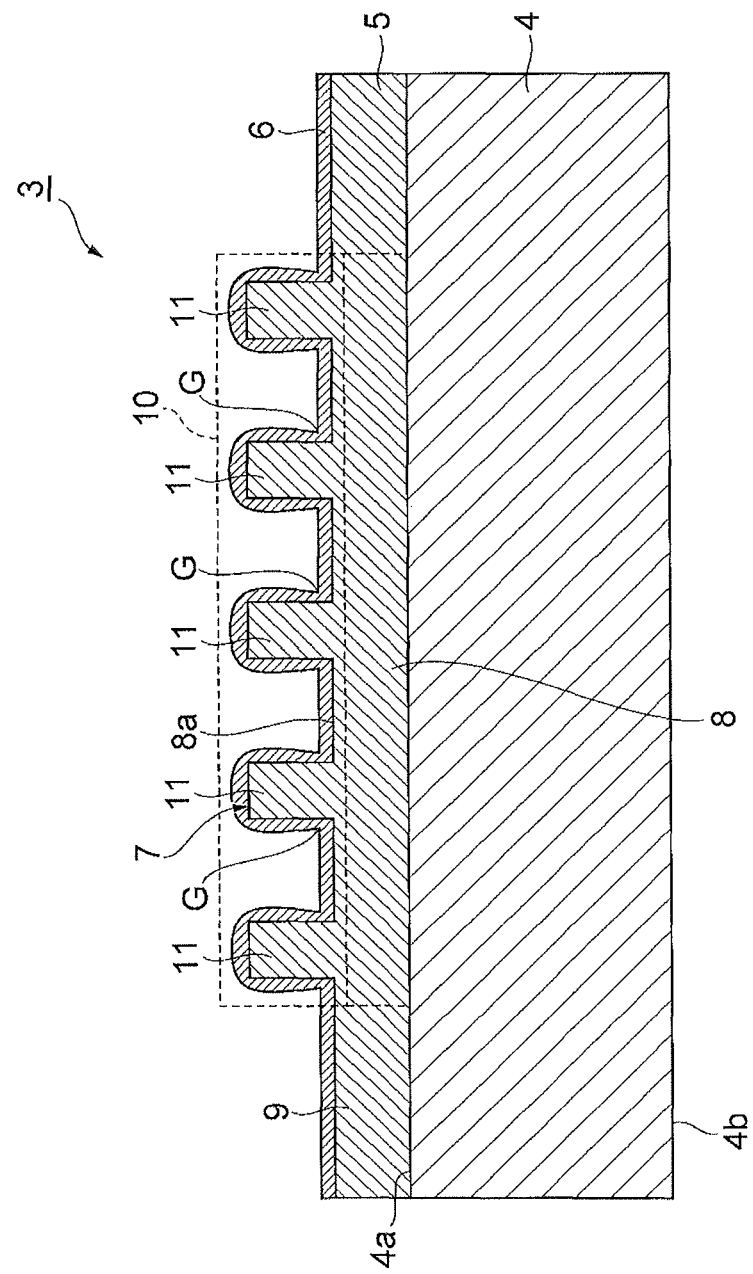
FIG. 3 is a vertical sectional view of an optical function part in the surface-enhanced Raman scattering element of FIG. 1.

As illustrated in FIG. 3, the molded layer 5 includes a fine structure part 7, a support part 8, and a frame part 9. The fine structure part 7, which is a region having a periodic pattern, is formed on a surface layer on the side opposite from the substrate 4 at a center part of the molded layer 5. In the fine structure part 7, a plurality of circular columnar pillars (projections) 11, each having a diameter and height on the order of several nm to several hundred nm, are periodically arranged at a pitch on the order of several ten nm to several hundred nm (preferably 250 nm to 800 nm) along a front face (principal surface) 4a of the substrate 4. The fine structure part 7 has a rectangular outer form on the order of several mm×several mm when seen in the thickness direction of the substrate 4. The support part 8, which is a rectangular region supporting the fine structure part 7, is formed on the front face 4a of the substrate 4. The frame part 9, which is a rectangular ring-shaped region surrounding the support part 8, is formed on the front face 4a of the substrate 4. The support part 8 and frame part 9 have a thickness on the order of several ten nm to several ten μm. The molded layer 5 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 4 by nanoimprinting, for example.

The conductor layer 6 is formed over the fine structure part 7 and frame part 9. In the fine structure part 7, the conductor layer 6 reaches a surface 8a of the support part 8 which is exposed to the side opposite from the substrate 4. The conductor layer 6 has a thickness on the order of several nm to several μm. The conductor layer 6 like this is formed by vapor-depositing a conductor such as a metal (Au, Ag, Al, Cu, Pt, or the like) on the molded layer 5 molded by nanoimprinting, for example. In the SERS element 3, the conductor layer 6 formed on the fine structure part 7 and the surface 8a of the support part 8 constructs an optical function part 10 which generates surface-enhanced Raman scattering.

Figure 4:
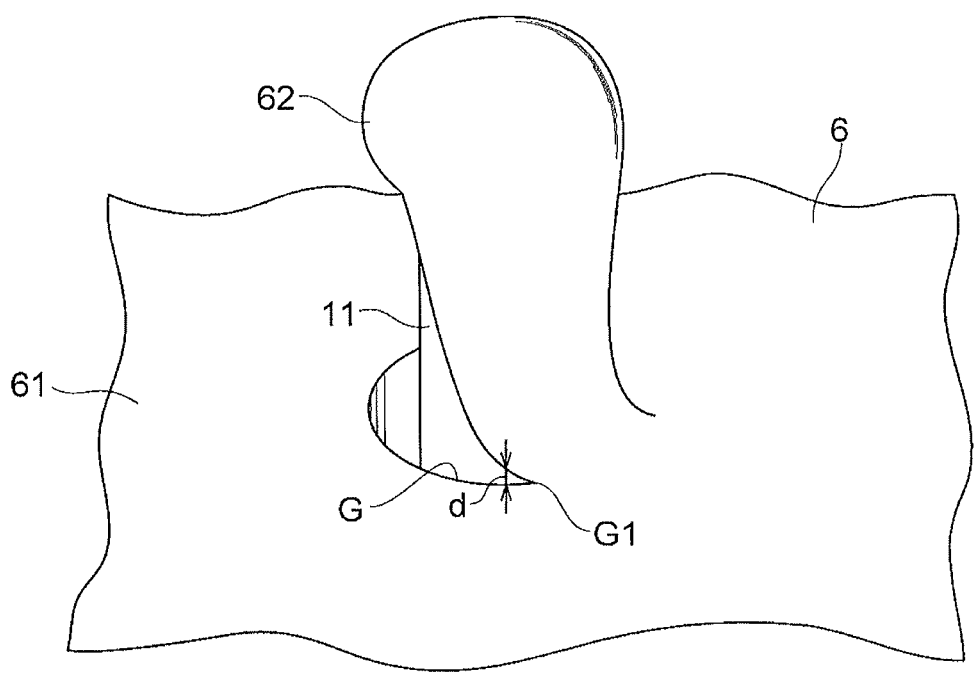
FIG. 4 is a perspective view of a pillar and a conductor layer in the optical function part of FIG. 3.
Figure 5:
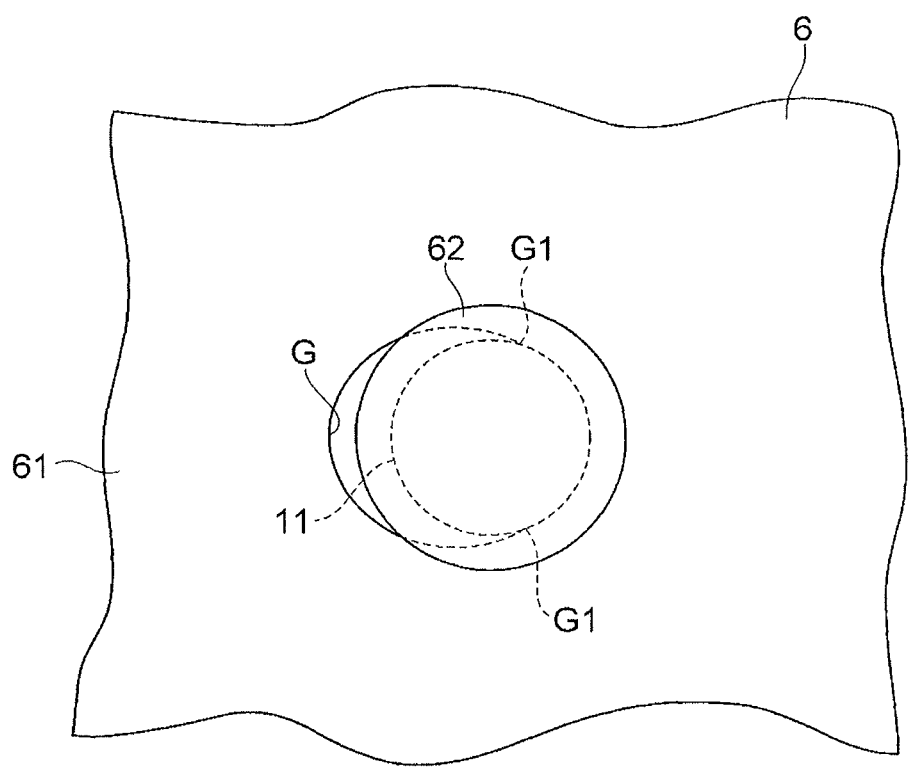
FIG. 5 is a plan view of the pillar and conductor layer in a modified example of the optical function part of FIG. 3.

As illustrated in FIGS. 4 and 5, the conductor layer 6 has a base part 61 formed along the front face 4a of the substrate 4 and a plurality of protrusions 62 protruding from the base part 61 at respective positions corresponding to the pillars 11. The base part 61 is formed like a layer on the surface 8a of the support part 8. The base part 61 has a thickness on the order of several nm to several hundred nm, which is smaller than the height of the pillars 11. Each protrusion 62 is formed so as to cover its corresponding pillar 11 in a state a part of the pillar 11 is exposed and has a form constricted at least at an end part on the substrate 4 side.

In the conductor layer 6, the base part 61 and protrusions 62 form a plurality of gaps G in which an interstice d in the projecting direction of the pillars 11 gradually decreases. The gap G has the interstice d on the order of 0 to several hundred nm. When seen in the projecting direction of the pillar 11, the gap G is formed into a crescent shape along a part of its corresponding pillar 11, while the interstice d of the gap G gradually decreases continuously at its both end parts G1. That is, the interstice d of the gap G in the projecting direction of the pillar 11 gradually becomes smaller toward the both ends. Here, the gaps G are arranged on the same side of their corresponding pillars 11.

The thickness of the base part 61 may be greater than the height of the pillar 11, and the protrusion 62 may be formed on an extension of its corresponding pillar 11. In the conductor layer 6, the base part 61 and protrusion 62 form the gap G gradually decreasing the interstice d in the projecting direction of the pillar 11 in this case as well.

The SERS unit 1 constructed as in the foregoing is used as follows. First, a ring-shaped spacer made of silicone, for example, is arranged on the front face 2a of the handling board 2 so as to surround the SERS element 3. Subsequently, a sample of a solution (or a dispersion of a powder sample in a solution such as water or ethanol) is dropped to the inside of the spacer with a pipette or the like, so as to arrange the sample on the optical function part 10. Then, for preventing the solvent from evaporating and for reducing the lens effect, a glass cover is mounted on the spacer and brought into close contact with the solution sample.

Next, the SERS unit 1 is set in a Raman spectroscopic analyzer, and the sample arranged on the optical function part 10 is irradiated with excitation light through the glass cover. This generates surface-enhanced Raman scattering at the interface between the optical function part 10 and sample, whereby surface-enhanced Raman scattering light derived from the sample is enhanced and released. Hence, the Raman spectroscopic analyzer enables Raman spectroscopy with high accuracy.

Not only the above-mentioned method, but the following methods may also be used for arranging the sample on the optical function part 10. For example, while holding the handling board 2, the SERS element 3 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 10 and left to dry. A powder sample may be dispersed as it is on the optical function part 10.

An example of methods for manufacturing the SERS element 3 will now be explained. First, as illustrated in (a) of FIG. 6, a master mold MM and a film base F are prepared. The master mold MM includes a fine structure part M7 corresponding to the fine structure part 7 and a support part M8 for supporting the fine structure part M7. A plurality of fine structure parts M7 are arranged in a matrix on the support part M8. Subsequently, as illustrated in (b) of FIG. 6, the film base F is pressed against the master mold MM and pressurized and heated in this state, so as to transfer a pattern of the plurality of fine structure parts M7 to the film base F. Then, as illustrated in (c) of FIG. 6, the film base F is released from the master mold MM, so as to yield a replica mold (replica film) RM having the pattern of the plurality of fine structure parts M7 transferred thereto. The replica mold RM may also be one formed by applying a resin (examples of which include resins based on epoxy, acrylics, fluorine, silicone, and urethane and inorganic/organic hybrid resins) onto the film base F. When the resin to be applied onto the film base F is UV-curable, the replica mold R can be obtained by curing the resin applied on the film base F by irradiation with UV (UV nanoimprinting) instead of thermal nanoimprinting.

Next, as illustrated in (a) of FIG. 7, a silicone wafer 40 to become the substrate 4 is prepared, and a UV-curable resin is applied onto a front face 40a of the silicon wafer 40, so as to form a nanoimprinting layer 50 to become the molded layer 5 on the silicone wafer 40. Subsequently, as illustrated in (b) of FIG. 7, the replica mold RM is pressed against the nanoimprinting layer 50, and the nanoimprinting layer 50 is irradiated with UV in this state, so as to be cured, whereby the pattern of the replica mold RM is transferred to the nanoimprinting layer 50. Then, as illustrated in (c) of FIG. 7, the replica mold RM is released from the nanoimprinting layer 50, so as to yield the silicone wafer 40 formed with a plurality of fine structure parts 7.

Next, a film of a metal such as Au or Ag is produced on the molded layer 5 by vapor deposition, so as to form the conductor layer 6. Subsequently, the silicone wafer 40 is cut for each fine structure part 7 (i.e., for each optical function part 10), whereby a plurality of SERS elements 3 are obtained. For yielding the SERS unit 1, it is sufficient for the SERS element 3 manufactured as mentioned above to be attached onto the handling board 2.

The fine structure part 7 may be formed on the substrate 4 by etching using a mask having a two-dimensional pattern formed by photoetching, electron beam lithography, or the like instead of the above-mentioned nanoimprinting. In either case, forming the conductor layer 6 on the fine structure part 7 by vapor deposition can produce the conductor layer 6 with the nano-order gaps G with a favorable reproducibility in a simple process, thereby enabling mass production of the SERS element 3.

In the conductor layer 6 constituting the optical function part 10 in the SERS element 3, a plurality of gaps G in which the interstice d in the projecting direction of the pillar 11 gradually decreases are formed by the base part 61 and protrusions 62 as explained in the foregoing. The gaps G formed in the conductor layer 6 favorably function as nanogaps (in particular in a part where the interstice d of the gaps G is 20 nm or less) where electric fields are locally enhanced. Therefore, the SERS element 3 can increase the intensity of surface-enhanced Raman scattering by favorable nanogaps.

Since a plurality of pillars 11 are arranged periodically along the front face 4a of the substrate 4, the intensity of surface-enhanced Raman scattering can be increased.

When seen in the projecting direction of the pillars 11, each gap G is formed along a part of its corresponding pillar 11 and gradually decreases the interstice d at its both end parts G1, whereby the gaps G favorably functioning as nanogaps can be increased.

Since the gaps G are arranged on the same side of their corresponding pillars 11, the intensity of light having a predetermined polarization direction can selectively be increased.

Since the interstice d of the gap G gradually decreases continuously, the gap G can securely function as a nanogap.

When the protrusion 62 has a form constricted at the end part on the substrate 4 side and is in contact with the base part as in this example, the gap G gradually decreasing the interstice d in the projecting direction of the pillar 11 can be obtained easily and securely.

Figure 8:
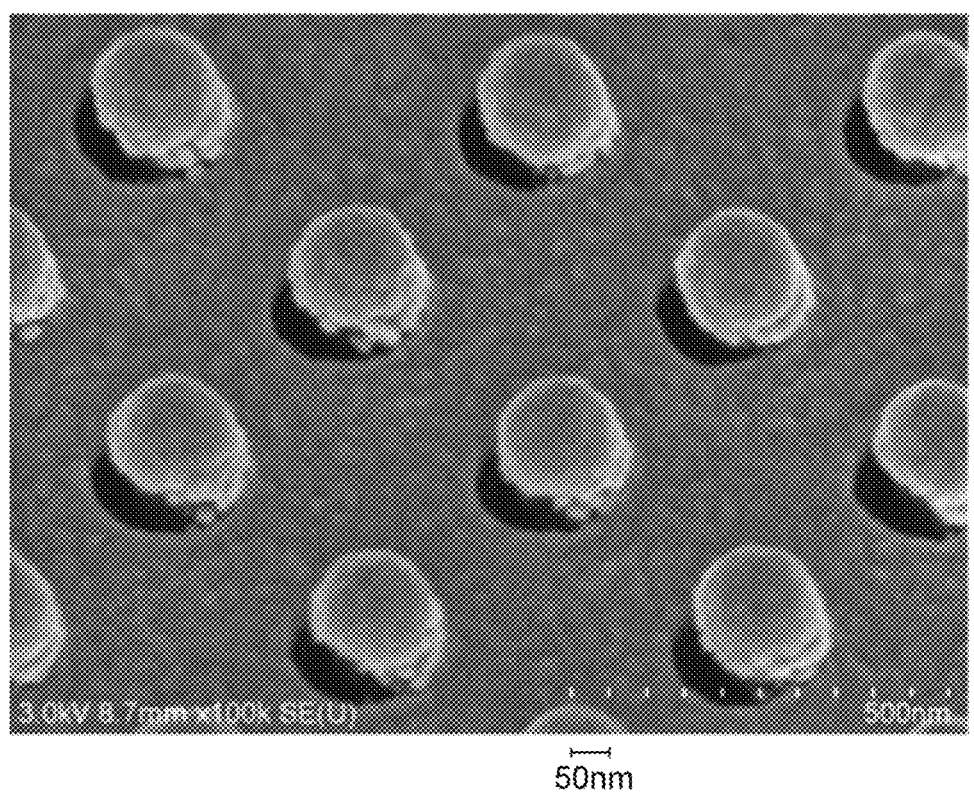
FIG. 8 is a SEM photograph of the optical function part in the surface-enhanced Raman scattering element of Example 1.

Examples of the SERS element 3 having the pillar 11 and conductor layer 6 illustrated in FIGS. 4 and 5 will now be explained. FIG. 8 is a SEM photograph of the optical function part in the SERS element of Example 1. FIG. 8 is a SEM photographs capturing the optical function part in a direction tilted by 30° from a direction perpendicular to the surface of the substrate.

The SERS element of Example 1 was made as follows. First, using a mold in which holes, each having a hole diameter of 120 nm and a hole depth of 200 nm, were arranged in a square lattice at a hole interval (distance between center lines of holes adjacent to each other) of 360 nm, a resin on a substrate made of glass was molded by nanoimprinting, so as to produce a fine structure part. In thus produced fine structure part, the pillars had a diameter of 120 nm, a height of 180 nm, and a pillar pitch (distance between center lines of pillars adjacent to each other) of 360 nm.

Next, a film of Ti was formed as a buffer layer by resistance heating vacuum vapor deposition on the produced fine structure part. The film forming condition for the buffer layer was "film thickness: 2 nm; vapor deposition rate: 0.02 nm/s; degree of vacuum during film forming: $2 \times 10^{-5}$ torr; substrate tilting angle: 20°; substrate rotation: none; substrate temperature control: none." Subsequently, a film of Au was formed as a conductor layer by resistance heating vacuum vapor deposition on the buffer layer, so as to yield the SERS element of Example 1. The film forming condition for the conductor layer was "film thickness: 50 nm; vapor deposition rate: 0.02 nm/s; degree of vacuum during film forming: $1.5 \times 10^{-5}$ torr; substrate tilting angle: 20°; substrate rotation: none; substrate temperature control: none."

Here, as illustrated in (a) and (b) of FIG. 9, the substrate tilting angle: θ means that the substrate 4 is arranged with respect to a vapor deposition source 100 such that a vapor deposition direction D1 of the vapor deposition source 100 and a direction D2 perpendicular to the front face 4a of the substrate 4 form the angle θ therebetween. In the SEM photograph of FIG. 8, the vapor deposition was performed from the right front side of FIG. 8, whereby the gaps open on the left side of the pillars.

Figure 10:
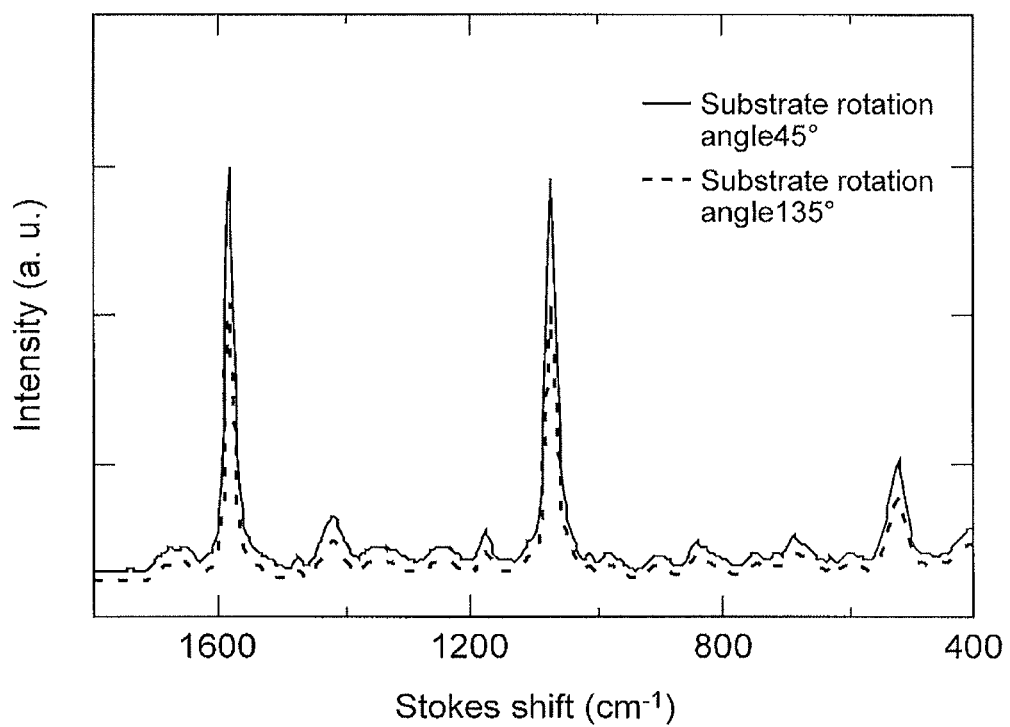
FIG. 10 is a graph illustrating a relationship between Stokes shift and signal intensity concerning the surface-enhanced Raman scattering element of Example 1.
Figure 11:
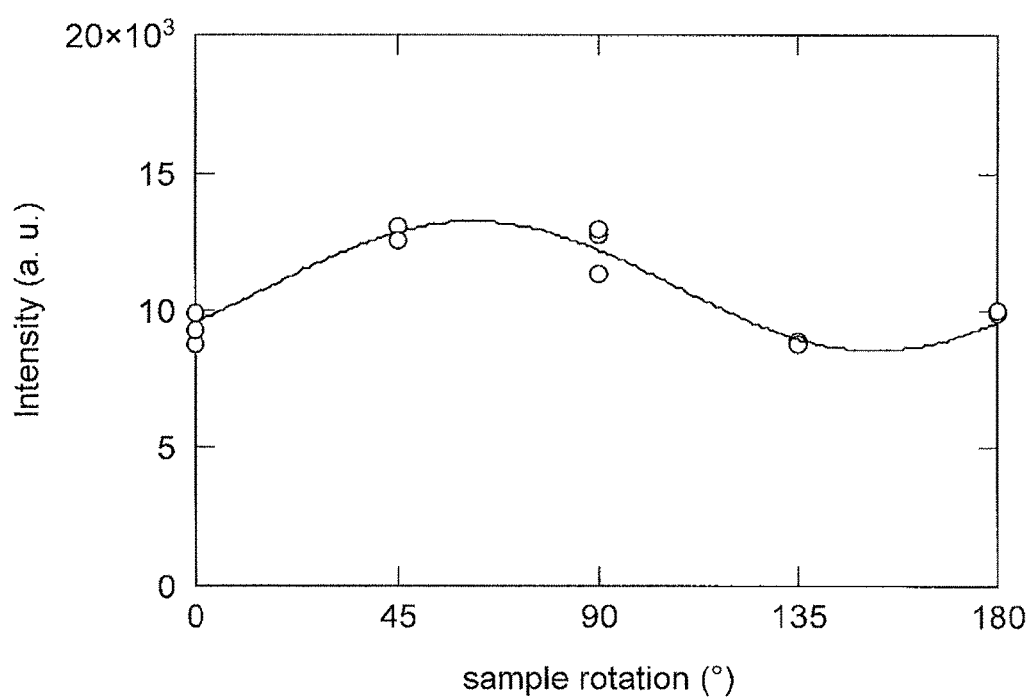
FIG. 11 is a graph illustrating a relationship between substrate rotation angle and signal intensity concerning the surface-enhanced Raman scattering element of Example 1.

FIG. 10 is a graph illustrating a relationship between Stokes shift and signal intensity concerning the SERS element of Example 1, while FIG. 11 is a graph illustrating a relationship between substrate rotation angle and signal intensity concerning the SERS element of Example 1. Here, the SERS element of Example 1 was dipped in an ethanol solution of mercaptobenzonic acid (1 mM) for two hours, then rinsed with ethanol, and dried with a nitrogen gas, so that a sample was arranged on the optical function part of the SERS element. While rotating the substrate about a center line perpendicular to the front face of the substrate by increments of 45°, the sample was subjected to Raman spectrometry with excitation light having a wavelength of 785 nm at the respective substrate rotation angles (i.e., 0°, 45°, 90°, 135°, and 180°).

As a result, a SERS spectrum of mercaptobenzonic acid was obtained at each of the substrate rotation angles of 45° and 135° as illustrated in FIG. 10. It is seen from FIG. 11, which illustrates results concerning a peak intensity at a Stokes shift of 1072 cm$^{-1}$ in the case of FIG. 10, that the signal intensity varies according to the substrate rotation angle, whereby the dependency on polarization direction occurs when the gaps are arranged on the same side of the respective pillars 11. Here, the polarization direction of excitation light and the arrangement direction of gaps with respect to the pillars coincide with each other when the substrate rotation angles is 45°.

Figure 12:
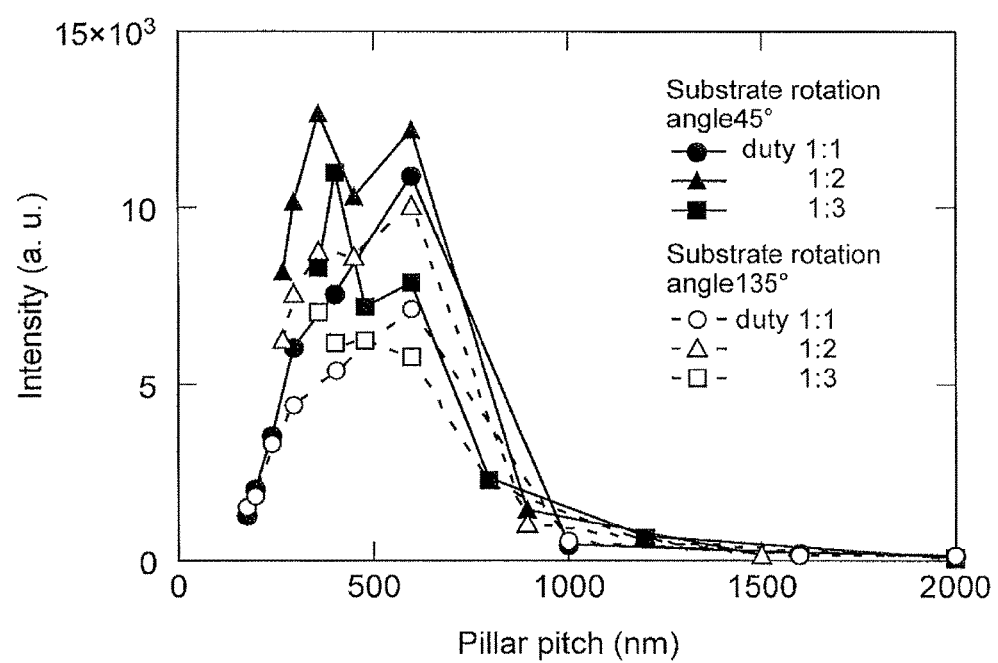
FIG. 12 is a graph illustrating a relationship between pillar pitch and signal intensity concerning the surface-enhanced Raman scattering element of Example 1.

FIG. 12 is a graph illustrating a relationship between pillar pitch and signal intensity concerning the surface-enhanced Raman scattering element of Example 1. This graph illustrates results concerning the peak intensity at the Stokes shift of 1072 cm$^{-1}$ in the case of FIG. 10. It is seen from FIG. 12 that the intensity of surface-enhanced Raman scattering depends on the pillar pitch (distance between the center lines of the pillars adjacent to each other) at each of the substrate rotation angles 45° and 135°, whereby the pillar pitch is preferably 250 nm to 800 nm in order to increase the intensity of surface-enhanced Raman scattering. These plots are substantially applicable even when the diameter of pillars varies. By "duty" in the graph of FIG. 12 is meant the ratio between the pillar width and the space between pillars in the fine structure part.

Figure 13:
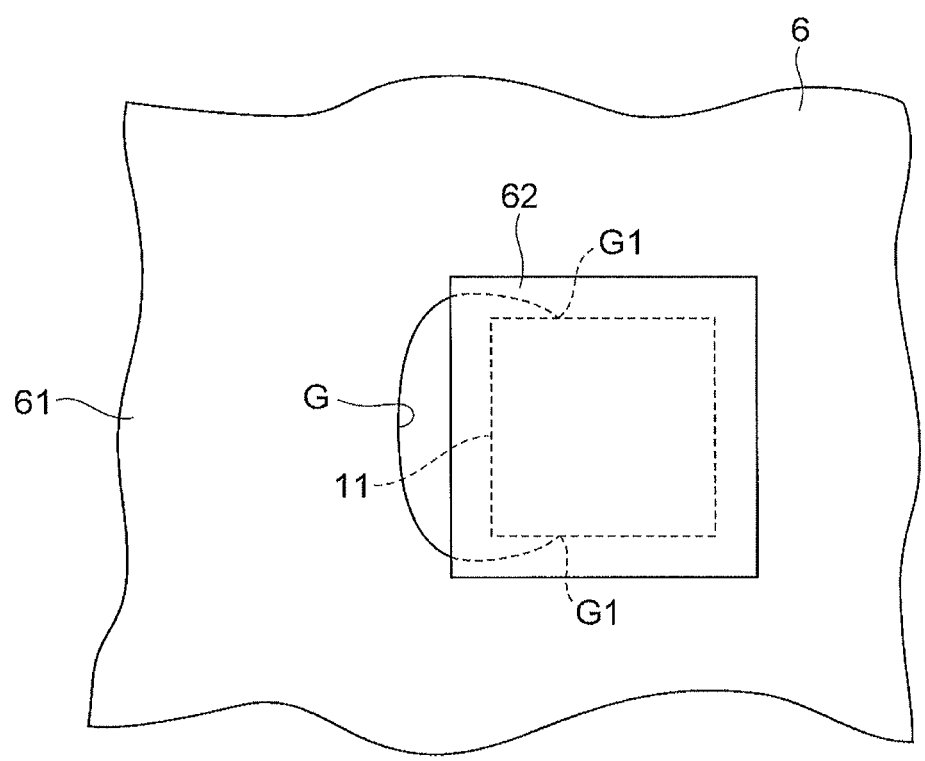
FIG. 13 is a plan view of the pillar and conductor layer in a modified example of the optical function part of FIG. 3.

While an embodiment of the present invention is explained in the foregoing, the present invention is not limited to the above-mentioned embodiment. For example, the pillars 11 may be arranged one-dimensionally instead of two-dimensionally or in a triangular lattice instead of a square lattice. The cross-sectional form of the pillars 11 is not limited to circles, but may be ellipses or polygons such as triangles and quadrangles. By way of example, as illustrated in FIG. 13, the base part 61 and protrusion 62 form the gap G gradually decreasing the interstice d in the projecting direction of the pillar 11 in the conductor layer 6 when the pillar 11 has a quadrangular cross section form as in the case where the pillar 11 has a circular cross section. When seen in the projecting direction of the pillars 11, the gap G is formed along a part of the pillar 11 and gradually decreases the interstice d continuously at its both end parts G1 in this case as well. As in the foregoing, without being restricted to those mentioned above, various materials and forms can be employed for constituents of the SERS element 3 and SERS unit 1.

When attention is focused on a pair of projections (those corresponding to the pillars 11) adjacent to each other, the width of the gap formed by the base part and the protrusion is smaller than the distance between the conductor layer formed on the outer surface of one projection and that formed on the outer surface of the other projection. This can easily and stably form such a narrow gap (gap favorably functioning as a nanogap) as to be unattainable by the configuration of the fine structure part alone.

The fine structure part 7 may be formed on the front face 4a of the substrate 4 either indirectly with the support part 8, for example, interposed therebetween as in the above-mentioned embodiment or directly. The conductor layer 6 may be formed on the fine structure part 7 either indirectly with a layer such as a buffer metal (Ti, Cr, or the like) for improving the adhesion of a metal to the fine structure part 7, for example, interposed therebetween or directly.

The thickness of the base part 61 may be either smaller than the height of the pillar 11 as in the above-mentioned embodiment or greater than the latter. Either configuration can increase the intensity of surface-enhanced Raman scattering by a favorable nanogap.

INDUSTRIAL APPLICABILITY

The present invention can provide a surface-enhanced Raman scattering element which can increase the intensity of surface-enhanced Raman scattering by a favorable nanogap.

REFERENCE SIGNS LIST

3: SERS element (surface-enhanced Raman scattering element); 4: substrate; 4a: front face (principal surface); 6: conductor layer; 7: fine structure part; 10: optical function part; 11: pillar (projection); 61: base part; 62: protrusion; G: gap.

The invention claimed is:
1. A surface-enhanced Raman scattering element comprising:
   a substrate having a principal surface;
   a fine structure part formed on the principal surface and having a plurality of projections; and
   a conductor layer formed on the fine structure part and constituting an optical function part for generating surface-enhanced Raman scattering;
   wherein the conductor layer has a base part formed along the principal surface and a plurality of protrusions protruding from the base part at respective positions corresponding to the projections; and
   wherein the base part and the protrusions form a plurality of gaps in the conductor layer, each of the gaps being formed by the base part and a protrusion of the plurality of protrusions, and each of the gaps having an interstice gradually decreasing downward in the projecting direction of the projection towards the base part, the gaps are formed along a circumferential direction of the projections and each of the gaps has two end parts when seen in the projecting direction of the projections, the interstice in the projecting direction of the projections gradually decreases downward in the projecting direction at least at one end part of the two end parts, and each gap has a terminus where the interstice becomes zero at a position where the base part and the protrusion intersect.

2. A surface-enhanced Raman scattering element according to claim 1, wherein the projections are arranged periodically along the principal surface.

3. A surface-enhanced Raman scattering element according to claim 1, wherein the gaps are formed along a part of the respective projections and each of the gaps have the interstice gradually decreasing at both end parts when seen in the projecting direction of the projections downward towards the base part.

4. A surface-enhanced Raman scattering element according to claim 3, wherein the gaps are arranged on the same side of the projections corresponding thereto.

5. A surface-enhanced Raman scattering element according to claim 1, wherein the interstice of the gap gradually decreases continuously.

6. A surface-enhanced Raman scattering element according to claim 1, wherein the protrusion has a form constricted at an end part on the substrate side.

7. A surface-enhanced Raman scattering element according to claim 1, wherein the base part has a thickness smaller than a height of the projections.

8. A surface-enhanced Raman scattering element according to claim 1, wherein the base part has a thickness greater than a height of the projections.

* * * * *